(12) United States Patent
Olmstead

(10) Patent No.: US 9,387,236 B2
(45) Date of Patent: Jul. 12, 2016

(54) PHARMACEUTICAL COMPOSITIONS CONTAINING PROTEASE AND METHODS FOR THE TREATMENT OF LYSOSOMAL STORAGE DISEASES

(75) Inventor: Stephen F. Olmstead, Reno, NV (US)

(73) Assignee: PROTHERA Inc., Reno, NV (US)

( * ) Notice: Subject to any disclaimer, the term of this patent is extended or adjusted under 35 U.S.C. 154(b) by 0 days.

(21) Appl. No.: 13/067,581

(22) Filed: Jun. 10, 2011

(65) Prior Publication Data

US 2012/0315263 A1    Dec. 13, 2012

(51) Int. Cl.
*C12Q 1/37*   (2006.01)
*A61K 38/48*   (2006.01)

(52) U.S. Cl.
CPC .............. *A61K 38/4813* (2013.01); *C12Q 1/37* (2013.01); *C12Y 304/14005* (2013.01); *G01N 2800/385* (2013.01)

(58) Field of Classification Search
CPC combination set(s) only.
See application file for complete search history.

(56) References Cited

U.S. PATENT DOCUMENTS

2002/0006400 A1* 1/2002 Lobel ........................ 424/94.1

OTHER PUBLICATIONS

Beck, "New therapeutic options for lysosomal storage disorders: enzyme replacement, small molecules and gene therapy" (2007) Human Genetics, vol. 121, 1-22.*
Beck, "Critical Review: Therapy for Lysosomal Storage Disorders" (2010) IUBMB Life, vol. 62, 33-40.*
Klaire Labs, SerenAid, 1 page, downloaded on Mar. 23, 2014 from http://www.klaire.com/prod/proddetail.asp?id=S123-C180.*

* cited by examiner

*Primary Examiner* — Robert Yamasaki
*Assistant Examiner* — Teresa E Knight
(74) *Attorney, Agent, or Firm* — Isaac Angres

(57) ABSTRACT

The invention provides a method and compositions for treating a subject with a lysosomal storage disease such as gaucher disease, by administering to a subject with a lysosomal storage disease a therapeutically effective amount of composition comprising at least one of a protease or peptidase in an amount sufficient to ameliorate, reduce or improve at least one symptom of the disease. The invention also provides dietary supplements for subjects having lysosomal storage diseases.

12 Claims, No Drawings

PHARMACEUTICAL COMPOSITIONS CONTAINING PROTEASE AND METHODS FOR THE TREATMENT OF LYSOSOMAL STORAGE DISEASES

FIELD OF INVENTION

This invention is related to the area of lysosomal storage diseases. The instant invention also relates to compositions and methods for enzyme replacement therapy of lysosomal storage diseases. In particular, the present invention provides methods and compositions for preventing and/or treating Gaucher's disease.

BACKGROUND OF THE INVENTION

The lysosome is a cytoplasmic organelle that functions to degrade macromolecules such as proteins, polynucleotides, polysaccharides, and lipids. The lysosome encloses an acidic environment and contains hydrolase enzymes which catalyze the hydrolysis of biological macromolecules. The lysosome has also been found to play a role in the uptake of molecules via endocytosis.

Lysosomal storage diseases occur when a lysosomal protein is deficient or mutant. In many cases, this protein is an enzyme, and abnormal deposits of the substrate of the deficient enzyme accumulate in the cell. In other cases, the deficient protein is involved in trafficking, post-translational processing, or protection or activation of a lysosomal enzyme. In still other cases, the defective protein is not an enzyme but exists in the intra-lysosomal space or spans the lysosomal membrane. The function of some of these proteins is presently unknown. There is extensive clinical and biochemical heterogeneity within the lysosomal storage diseases, which include most of the lipid storage disorders, the mucopolysaccharidoses, the mucolipidoses, and glycoprotein storage diseases. Currently there are approximately 50 lysosomal storage disorders known including Niemann-Pick disease, Fabry's disease, Gaucher disease, etc. The disorders are typically progressive and frequently are fatal in childhood or adolescence. Genetic counseling is important in the management of these diseases, and specific therapies such as enzyme replacement therapy are promising but expensive. Typically the care for these patients is largely symptomatic.

Lysosomal storage disorders (LSDs) are a group of approximately 50 inherited metabolic diseases that result from cellular deficiencies of a specific lysosomal enzyme, receptor target, activator protein, membrane protein, or transporter that leads to pathogenic accumulation of substances in lysosomes, causing buildup of the substrate, resulting in deterioration of cellular and tissue function. The hallmark feature of LSDs is the abnormal accumulation of metabolites in the lysosomes which leads to the formation of large numbers of distended lysosomes in the perikaryon. A major challenge to treating LSDs (as opposed to treating an organ specific enzymopathy, e.g., a liver-specific enzymopathy) is the need to reverse lysosomal storage pathology in multiple separate tissues. Lysosomal storage disorders occur in approximately 1 in 5,000 to 1 in 10,000 live births and display considerable clinical and biochemical heterogeneity. The majority of lysosomal storage disorders are inherited as autosomal recessive conditions although two examples of X-linked are Hunter syndrome (MPS II) and Fabry disease. The extent and severity of the lysosomal storage disorder depend on the type and amount of substrate that accumulates, but almost all disorders are progressive. Most disorders have both central nervous system and systemic manifestations, whereas some affect either just the central nervous system or tissues outside the nervous system. Many patients with lysosomal storage disorders die in infancy or childhood, and patients who survive to adulthood often have a decreased lifespan and significant morbidity. Examples of lysosomal disorderes include defective metabolism of mucopolysaccharides (MPS) I-IX (Hurler, Scheie, Hunter, Sanfilippo, Morquio, glycosaminoglycans Maroteaux-Lamy, Sly diseases, hyaluronidase deficiency), defective degradation of glycan aspartylglucosaminuria, fucosidosis, mannosidosis, glucosphingolipids Schindler disease, sialidosis type I, defective degradation of glycogen (Pompe disease), defective degradation of globotriaosylceramide (Fabry disease), defective degradation of lipids (Farber disease), Gaucher disease (types sphingolipid components 1-3) GM1-gangliosidosis, GM2-gangliosidoses (Tay-Sachs disease, Sandhoff disease, GM2 activator disease), Krabbe disease, metachromatic leukodystrophy, Niemann-Pick disease (type A or B), pycnodysostosis, defective degradation or transport of lipofuscins causing ceroid lipofuscinosis (multiple types with different of cholesterol, cholesterol esters, or defects, some not known yet), cholesterol ester storage disorders and other complex lipid storage diseases, Niemann-Pick disease type C, Wolman disease, deficiencies of multiple lysosomal sulfatases, galactosialidosis, mucolipidosis types I, III and IV, cystinosis, sialic acid storage disorder, Marinesco-Sjogren syndrome, Hermansky-Pudlak syndrome (several forms), Chediak-Higashi syndrome, and Danon disease.

Gaucher disease is the most prevalent lysosomal storage disorder and results from the deficiency of glucocerebrosidase (GC; EC 3.2.1.45) in all tissues. This enzyme deficiency results in accumulation of glucosylceramide in lipid-laden macrophages (called Gaucher cells) in the reticulendothelial system including liver, spleen, lung, and bone marrow. Gaucher disease has been categorized into three major phenotypes: type 1, non-neuropathic; type 2, acute infantile neuropathic; and type 3, chronic neuropathic. The spectrum of illness severity for type 1 Gaucher disease is broad. Children and adults can be asymptomatic or may have severely debilitating symptoms, including skeletal degeneration, anemia, thrombocytopenia and hepatosplenomegaly. Symptoms can present at any age. Although type 1 Gaucher disease is more common among the Ashkenazi Jewish population, it occurs in all ethnic groups. Type 2 Gaucher disease is rapidly progressive. By six months of age, most type 2 infants have brainstem dysfunction and succumb to complications such as respiratory arrest or aspiration pneumonia at 18-24 months of age. Type 3 Gaucher disease patients develop neurological abnormalities at a later age than type 2 patients; most only develop a subtle horizontal saccadic eye movement defect.

Gaucher disease is the most common lysosomal storage disorder, affecting approximately 8,000 to 10,000 people worldwide. In Gaucher disease, the activity of a lysosomal enzyme, known as acid-beta-glucosidase or glucocerebrosidase (GlcCerase), is significantly decreased owing to one of approximately 200 mutations in the GBA gene that codes for the enzyme. This condition is inherited in an autosomal recessive pattern, which means that people with mutations in both copies of the GBA gene develop Gaucher disease. Reduced GlcCerase activity leads to the accumulation of glucocerebroside (also called glucosylceramide) in tissues, including the spleen, liver, lungs, bone marrow, and sometimes in the brain. This accumulation of glucocerebroside is believed to cause the various symptoms and signs of Gaucher disease, including an enlarged liver and spleen (splenomegaly), skeletal disorders, and, in some instances, lung, kidney, and central nervous system impairment. There is also an association between Gaucher disease and Parkinson disease or Parkinson-like disorders that affect movement and balance (parkinsonism). Parkinsonism has been observed in patients with Gaucher disease and in disease gene carriers (Lesage et al., 2011). The signs and symptoms of parkinsonism in such persons may include: intention tremors, rigidity and bradykinesis, expressionless facies, slurred or monotonous speech, myoclonic jerks, olfactory loss, and avascular osteonecrosis (Neudorfer et al., 1996; Bultron et al., 2010). Lewy body dementia has also been reported in some subjects. Effective dietary and/or pharmaceutical interventions for one or more of these signs and symptoms would significantly improve the quality of life in such persons.

Currently, enzyme-replacement therapy (ERT) and substrate-reduction therapy are the only approved treatment options for patients with Gaucher disease (for a review see Harmanci, 2008). ERT, using recombinant imiglucerase, improves the visceral and hematologic manifestations of the disease, but it is not effective in neuropathic forms of Gaucher disease. Also, the cost of ERT is approximately $200,000 per year per patient, which is prohibitive for many patients, and there is insufficient supply of recombinant enzyme to meet the medical needs in the market place. Furthermore, recombinant imiglucerase must be administered intravenously, which is a disadvantage. The first oral therapeutic agent for Gaucher disease is miglustat (N-butyldeoxynojirimycin), an iminosugar inhibitor of glucosylceramide synthase, which is used for substrate-reduction therapy. Miglustat produces clinical improvement in selected patients with mild or moderate disease, but the responses are slower and less robust than those observed with ERT. Other potential therapies for Gaucher disease are still in development (Futerman, 2004).

There is a long felt need for methods to prevent and/or treat lysosomal storage disorders that provide patients with a higher quality of life and achieve a better clinical outcome. In particular, there is a need for methods to prevent and/or treat Gaucher's disease that provide patients with a higher quality of life and achieve a better clinical outcome.

Thus, there has gone unmet a long felt need for improved methods and compositions, for the treatment of Gaucher disease. In particular there has gone unmet a long felt need for methods and compositions, that are orally available and cost-effective. There remains a need for additional therapies to treat these often fatal diseases. The present systems, compositions and methods provide these unmet long felt needs as well as other advantages not provided by prior therapies.

OBJECTS OF THE INVENTION

Accordingly, it is an object of the present invention to provide novel therapeutic methods for treating lysosomal storage disorders.

Another object of the present invention is to provide protease/peptidase compositions for treating lysosomal storage disorders.

It is a further object of the instant invention to provide proteases/peptidases for the treatment of Gaucher disease.

A still further object of the invention is to provide a method for reducing the symptoms of Gaucher disease, A further object of the invention is the use of combination of proteases/peptidases to treat Gaucher disease.

These and other objects of the present invention will more readily become apparent from the description and examples which follow.

SUMMARY OF THE INVENTION

The present invention provides novel compositions and methods using the same to prevent and/or treat a lysosomal storage disorder in a patient at risk for developing or diagnosed with the same which includes administering to the patient in need thereof an effective amount of a compositions described herein.

The present invention further provides methods and compositions for treating lysosomal storage disease including, but not limited to, Pompe Disease, GM1 gangliosidosis, Tay-Sachs disease, GM2 gangliosidosis, Sandhoff disease, Fabry disease, Gaucher disease, metachromatic leukodystrophy, Krabbe disease, Niemann-Pick disease type A, Niemann-Pick disease type B, Niemann-Pick disease type C, Niemann-Pick disease type D, Farber disease, Wolman disease, Hurler Syndrome, Scheie Syndrome, Hurler-Scheie Syndrome, Hunter Syndrome, Sanfilippo A Syndrome, Sanfilippo B Syndrome, Sanfilippo C Syndrome, Sanfilippo D Syndrome, Morquio A disease, Morquio B disease, Maroteaux-Lamy disease, Sly Syndrome, α-mannosidosis, β-mannosidosis, fucosidosis, aspartylglucosaminuria, sialidosis, mucolipidosis II, mucolipidosis III, mucolipidosis IV, Goldberg Syndrome, Schindler disease, cystinosis, Salla disease, infantile sialic acid storage disease, Batten disease, infantile neuronal ceroid lipofuscinosis, or prosaposin.

The present invention also relates to therapeutic approaches to the treatment of lysosomal storage diseases, such as glycogen storage disease type II, mucopolysaccharidoses, mucolipidosis II, mucolipidosis III, mucosulfatidosis, GM2 activator protein deficiency variant AB, Danon disease, Salla disease, Tay-Sachs disease, Sandhoff disease, Schindler disease, Kanzaki disease, α-mannosidosis, β-mannosidosis, fucosidosis, sialidosis, aspartylglucosaminuria, carbohydrate-deficient glycoprotein syndrome, Wolman disease, Farber disease, Niemann-Pick disease types A, B, and C, Gaucher disease, Krabbe disease, Fabry disease, multiple sulfatase deficiency, GM1 gangliosidosis, GM2 gangliosidosis, GM3 gangliosidosis, galactosialidosis, cystinosis, sialic acid storage disease, pyknodysostosis, metachromatic leukodystrophy, galactosialidosis, neuronal ceroid lipofuscinosis (types 1-9), lactosylceramidosis, Pompe disease, and cobalamin definiciency type F, by treatment with at least one of a protease or peptidase in an amount sufficient to ameliorate, reduce or improve at least one symptom or marker of the lysosomal storage disease.

In one aspect, the compositions, methods, systems, herein are directed to providing physiologically-acceptable compositions that are capable of reducing one or more symptoms of Gaucher disease in individuals in need thereof, and methods of making and using or administering such compositions.

In another aspect, the compositions, capsules, methods, herein comprise compositions for reducing the at least one symptom of Gaucher disease in individuals in need thereof. In one embodiment, the at least one symptom of Gaucher disease that is reduced by the subject compositions, methods, etc. is one of the following signs or symptoms of the disease: skeletal abnormalities, including thinning of the bones (osteopenia), bone pain and bone fractures; enlarged liver (hepatomegaly) or spleen (splenomegaly), or both; a decrease in healthy red blood cells (anemia); excessive fatigue; a greater susceptibility to bruising, which may indicate a low number of blood platelets (thrombocytopenia); yellow spots in the eyes (pingueculae); delayed puberty—and/or nosebleeds; and cognitive deterioration. In a preferred embodiment of the invention, the symptom that is reduced is splenomegaly.

In a further aspect of the invention, surrogate markers of Gaucher disease are used for assessing the utility of the compositions for the treatment of Gaucher disease. Suitable disease markers include cellular, physiological or biochemical markers.

In a further embodiment, the physiologically acceptable compositions, formulations, methods, etc. can be used as dietary supplements or as food additives or as pharmaceutical agents or otherwise as desired to reduce symptoms of Gaucher disease. Oral administration is an advantage, because the oral route of administration of therapeutic agents is preferred to any other route.

These physiologically-acceptable compositions and methods may be used in conjunction with other therapies for Gaucher disease. For example, the compositions may be used in conjunction with enzyme replacement therapy (ERT) or substrate reduction therapy (SRT).

In another aspect, the present invention provides kits for the treatment of a lysosomal storage disease. The inventive kits include at least one protease or a pharmaceutical composition thereof for the treatment of a lysosomal storage disease. The kits may also include other agents for treating the underlying lysosomal storage disease or symptoms thereof as described herein. The kit typically includes multiple doses of one or more proteasese and an optional second therapeutic agent. The kit may include enough dosages of each agent for treating a subject for one week, two weeks, three weeks, one month, two months, three months, six months, or longer. The kit may also include devices for administering the agents such as a spoon, syringe, etc. The kit also typically includes prescribing information for the agents included in the kit.

The methods herein include methods, kits, labels and systems directed to labeling, marketing and otherwise providing the compositions to health care professionals and/or to consumers for use in reducing symptoms of Gaucher disease.

In an additional aspect of the invention, the physiologically acceptable proteolytic enzyme(s) may be found in a food or beverage that is suitable for human consumption. In one aspect, the physiologically-acceptable protease(s)/peptidase(s) are found in fermented foods.

In another aspect of the invention the physiologically acceptable protease or peptidase can be found in a food-grade microorganism, yeast, algae, or seaweed, -plant, vertebrate animal, invertebrate animal, annelid, insect, or arthropod.

In another embodiment, the physiologically acceptable enzyme is a peptidase or a protease-peptidase complex having prolyl oligopeptidase activity, dipeptidyl peptidase activity or tripeptidylpeptidase activity.

According to a further embodiment of this invention, the physiologically acceptable enzyme has DPP-IV aminopeptidase activity.

According to a further embodiment of this invention, the enzyme is an *Aspergillus* protease with DPP-IV aminopeptidase activity.

In a preferred aspect of the invention, the composition comprises SERENAID® a dietary supplement which has protease and DPP-IV activity among other ingredients.

In a further aspect of the invention, a protease or peptidase is given in combination with one or more of the following: vitamins, minerals, antioxidants, bioflavonoids, other enzymes, herbs, herbal extracts, plant and animal concentrates, probiotics, or other ingredients.

In yet another aspect of the invention, the methods, compositions etc. comprise two or more proteases or peptidases in a synergistic composition.

In one embodiment the product can be a kit or system wherein the compositions, capsules herein are contained in a pharmaceutically acceptable container and a written description, brochure, information sheet, catalog, or label explaining the product can reduce one or more symptoms of Gaucher disease. Further, the product can be marketed together with the written description, brochure, information sheet, catalog, or label explaining that the product can reduce one or more symptoms of Gaucher disease.

These and other aspects, features, and embodiments are set forth within this application, including the following detailed description. Unless expressly stated otherwise, all embodiments, aspects, features, etc., can be mixed and matched, combined, and permuted in any desired manner.

DESCRIPTION OF THE PREFERRED EMBODIMENTS

In its broadest aspects, the instant invention teaches the use of effective amounts of or more proteolytic enzyme that are physiologically acceptable for oral administration to reduce, improve or treat one or more symptoms of lysosomal storage diseases in mammals.

The instant invention teaches the use of effective amounts of proteolytic enzymes that are physiologically acceptable for oral administration to reduce, improve or treat one or more symptoms of Gaucher disease in mammals.

The present invention further teaches that proteolytic enzymes that are physiologically acceptable for oral administration can be used to reduce, improve or treat one or more symptoms of Gaucher disease in humans.

The present invention relates to therapeutic approaches to the treatment of lysosomal storage diseases, such as glycogen storage disease type II, mucopolysaccharidoses, mucolipidosis II, mucolipidosis III, mucosulfatidosis, GM2 activator protein deficiency variant AB, Danon disease, Salla disease, Tay-Sachs disease, Sandhoff disease, Schindler disease, Kanzaki disease, α-mannosidosis, β-mannosidosis, fucosidosis, sialidosis, aspartylglucosaminuria, carbohydrate-deficient glycoprotein syndrome, Wolman disease, Farber disease, Niemann-Pick disease types A, B, and C, Gaucher disease, Krabbe disease, Fabry disease, multiple sulfatase deficiency, GM1 gangliosidosis, GM2 gangliosidosis, GM3 gangliosidosis, galactosialidosis, cystinosis, sialic acid storage disease, pyknodysostosis, metachromatic leukodystrophy, galactosialidosis, neuronal ceroid lipofuscinosis (types 1-9), lactosylceramidosis, Pompe disease, and cobalamin definiciency type F, by treatment with a farnesyl transferase inhibitor.

In one aspect, the invention provides methods for treating a subject with a lysosomal storage disease by administering a therapeutically effective amount of a least one protease, peptidase, or protease/peptidase complex.

In another aspect, the invention provides methods for treating one or more symptoms or signs of Parkinson's disease in a subject with Gaucher disease or in a subject who is a carrier.

The inclusion of at least one protease, peptidase, or protease/peptidase complex is essential for the present invention.

Proteases are ubiquitous enzymes that are present in a wide variety of sources including plants, animals and microbes. They catalyze the hydrolytic cleavage of the peptide bond present in proteins and peptides. In the present invention the terms 'peptidase' and 'protease' are used interchangeably. Candidate proteases may be any pharmaceutically acceptable protease that produces a desired effect as described herein, given singly or in combination with vitamins, minerals, antioxidants, bioflavonoids, other enzymes, herbs, herbal extracts, plant and animal concentrates, probiotics, or other pharmaceutically active ingredients.

The identification and selection of proteases suitable for use in this invention can be achieved by empirical means. For example, suitable physiologically acceptable compositions that are the subject of the invention can be administered to individuals having Gaucher disease, and one or more symptoms or signs of Gaucher disease can be monitored to assess the efficacy of the composition in reducing said symptoms.

The symptoms or signs of Gaucher disease that may be monitored for improvement include one or more of the following: skeletal abnormalities, including loss of bone density (osteopenia), bone pain and bone fractures; enlarged liver (hepatomegaly) or spleen (splenomegaly), or both; a decrease in healthy red blood cells (anemia); excessive fatigue; a greater susceptibility to bruising, which may indicate a low number of blood platelets (thrombocytopenia); yellow spots in the eyes (pingueculae); delayed puberty; nosebleeds; and/or cognitive deterioration. In another aspect, in individuals with at least one Gaucher disease gene mutation associated with Parkinson's disease, one or more of the following disease symptoms or signs may be monitored for improvement: intention tremors, rigidity and bradykinesis, expressionless facies, slurred or monotonous speech, myoclonic jerks, olfactory loss, avascular osteonecrosis, and dementia.

The compositions, capsules, methods, etc. herein comprise compositions for reducing at least one symptom or sign of Gaucher disease, typically thereby effecting an improvement in the at least one symptom or sign. In a preferred embodiment of the invention, the sign that is reduced is splenomegaly.

Cellular, physiological and biochemical markers of Gaucher disease may also be useful for selecting optimal proteases for use in the invention. Potential disease markers can be found for example in US Patent Applications 2010/0196279, US Patent Appl 2010/0120056; and Lieberman, 1976).

Many proteases and peptidases are generally recognized as safe for human consumption, i.e., they are physiologically acceptable. Many sources can be found in the scientific and patent literature. For example, supplementary digestive enzyme formulations have been shown to improve nutrient absorption (U.S. Pat. No. 7,235,390), to reduce heartburn and indigestion (U.S. Pat. No. 7,067,124); to promote fast surgical recovery (U.S. Pat. No. 6,900,173); to improve airway mucus hypersecretory diseases (Rogers, 2007); and to improve liver function, cystic fibrosis, cholesterol absorption and gallstones (U.S. Pat. No. 5,324,514). Bromelain, a plant protease, has been used for the oral systemic treatment of inflammatory, blood-coagulation-related and malignant diseases (Maurer, 2001). Orally available proteases and peptidases have been used to maintain the basal level of cholecystokinin in blood plasma of a mammal and to treat abdominal pain in mammals suffering pancreatitis (U.S. Pat. No. 7,459,155). Many such enzymes not only retain their activity in the gut, but are absorbed intact through the gastrointestinal tract and retain activity in the bloodstream (see e.g. Castell et al., 1997; Fujita et al., 1995). For the purpose of the present invention, it is not necessary that the exact mechanism of action of the protease or peptidase be known so long as the desired effect is achieved.

Proteolytic enzymes that are physiologically acceptable can be found in certain bacteria, fungi, yeast and molds (Rao et al., 1998; Sumatha et al, 2006; Peng et al., 2005). For example, proteases and peptidases may be found in fungi, which have been used in the fermentation of many traditional foods and beverages. Suitable species include *Fusarium, Rhizopus, Actinomucor, Aspergillus*, and *Neurospora* species (see e.g.: U.S. Pat. No. 6,413,512; U.S. Pat. No. 3,932,618; US Patent Appl. 2009/0155239; Sriranganadane, et al., 2010; O'Toole, 1999; Kudryavtseva et al., 2008; Frish, 1974; Machida, 2010; Luisetti et al., 1991; Meyer et al., 2010; and Kolodny, 1963).

Proteases and peptidases also can be found in lactic acid bacteria, which are used to produce yogurt and other fermented dairy products (Liu et al., 2010). Nattokinase, seaprose, serratiopeptidase, pronase, fusarium protease, sfericase are examples of proteolytic enzymes that are physiologically acceptable (e.g. U.S. Pat. No. 5,296,223; Majima Y., et al., 1988; Pant K K, et al., 2008; Yoshida K, 1983; Sumi H, et al., 1990).

Prolyl oligopeptidases belong to a distinct class of serine peptidases (EC 3.4.21.26). These enzymes cleave peptide bonds at the carboxy-terminal side of proline residues. These peptidases have been implicated in such diseases and disorders as anxiety, psychotic and depressive disorders, cognitive disorders, pain perception, and neurodegenerative disorders such as Lewy body dementia, Parkinson's disease, and Huntington's disease (Goossens et al., 1996; Sedo et al., 1991; Mantle et al., 1996). Decreased levels of prolyl endopeptidase activity may also play a role in the pathophysiology of major depression (Maes et al., 1995). The distribution of prolyl oligopeptidases, and their potential for therapeutic discovery, was recently reviewed (Rosenblum et al., 2003). A prolyl aminopeptidase that removes N-terminal proline and hydroxyproline residues from peptides has been identified in *Aspergillus niger* (Basten et al., 2005).

Dipeptidyl aminopeptidases cleave a dipeptidyl moiety from the N-terminus of a polypeptide (Kreil, 1990). Dipeptidyl aminopeptidases of type IV (DPP IV) belong to a set of specialized proteases that are capable of cleaving bonds adjacent to prolines (Cunningham and O Connor 1997; Lambeir et al., 2003). This domain defines serine peptidases belonging to EC 3.4.14.5. The EC 3.4.14.5 enzyme class is widely used in the feeds, food processing, and dietary supplement industries. In humans, DPP-IV (also known as CD 26) is thought to be involved in psychoneuroendocrine function, nutrition, and immune defense (Hildebrandt et al., 2000). DPP-IV proteases can be found in variety of organisms, such as yeasts, fungi, insects, and frogs. An extracellular DPP-IV has been characterized from several *Aspergillus* species including *Aspergillus oryzae, Aspergillus niger* and *Aspergillus melleus* (Doumas et al. 1998, Tachi et al, 1992; Jalving et al., 2005).

Oral supplementation with prolyl endopeptidases has been proposed to treat adverse food reactions including the enteropathic manifestations of celiac disease or celiac sprue. Food-grade proteases capable of breaking down dietary gluten have been suggested to mitigate this problem (U.S. Pat. No. 7,741,094). Ehren et al. (2009) have proposed a combination of two food-grade enzymes, aspergillopepsin (ASP) from *Aspergillus niger* (EC 3.4.23.18) and dipeptidyl peptidase IV (DPP-IV) from *Aspergillus oryzae* (EC 3.4.21.63). Mitea et al. (2008) suggested that the co-administration of a prolyl endopeptidase with a gluten-containing meal might eliminate gluten toxicity. Byun et al. (2001) reported the synergistic action of an X-prolyl dipeptidyl aminopeptidase and a nonspecific aminopeptidase in protein hydrolysis. Synergistic compositions are also contemplated in the present invention.

Prolyl peptides, which are released during digestion of casein and gluten are believed to act as opioid receptor agonists, or exorphins, that may mediate or exacerbate neurobehavioral symptoms in individuals with autism spectrum disorders (ASD). These opioid-like peptides have been referred to as casomorphins and gluteomorphins. DPP-IV is also referred to as a casomorphinase because of its proteolytic activity against casomorphins. Supplemental DPP-IV has been proposed for the reduction of the symptoms of ASD (U.S. Pat. Nos. 6,251,391; 6,413,512; 6,447,772; 6,808,708; 6,821,514; 6,899,876).

Tripeptidyl peptidases, or sedolisins, are widespread among filamentous ascomycetes including *Aspergillus* species (Reichard et al., 2006; Gotou et al., 2009). In humans, mutations in the gene that encodes tripeptidyl-peptidase I causes late infantile neuronal ceroid lipofuscinosis, a fatal neurodegenerative disease (Pal et al., 2009), but the activity of tripeptidyl-peptidase I in Gaucher disease has not been reported.

Although many proteolytic enzymes have been shown to be physiologically acceptable for use in humans, as discussed herein, none of the above references anticipate the use of proteases or peptidases in compositions for the treatment of Gaucher disease.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular protease or peptidase of the present invention employed, or derivatives thereof, oral administration, the time of administration, the rate of excretion or metabolism of the particular protease being employed, the duration of the treatment, other drugs, compounds and/or materials used in combination with the particular proteases employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician could start doses of the proteases or peptidases of the invention employed in the pharmaceutical composition at levels lower than that required to achieve the desired therapeutic effect and then gradually increasing the dosage until the desired effect is achieved.

The following examples further describe and demonstrate embodiments within the scope of the present invention. These examples are solely for the purpose of illustration and are not to be construed as limitations of the present invention as many variations are possible without departing from the spirit or scope thereof.

EXAMPLE 1

A product known as SERENAID® is a blend of six plant-derived enzymes including a protease with dipeptidyl peptidase IV (DPP-IV) activity (see e.g. U.S. 6,251,391). SERENAID® is formulated to assist in breaking down plant and animal proteins, including casein (milk and dairy products), gluten (wheat, rye, oats, barley, and other grains), and soy proteins. We have observed a reduction in splenomegaly and increased energy in patients with Gaucher disease, following the initiation of oral administration of SERENAID®. The present invention contemplates the use of SERENAID® to improve one or more symptoms, signs, or markers of Gaucher disease in individuals in need thereof.

An exorphin-inhibiting composition was created comprising casomorphinasa (having DPP IV activity) and gluteomorphinasa, having the following components. Peptidase FPII, having an activity of 25,000 HUT (hemoglobin units of tyrosine; National Enzyme Company, Forsythe, Mo., USA 65653, and from Valley Research, Inc., South Bend, Ind., USA 46624 as Validase® FP) and comprising casomorphinase (having DPP IV activity). It was produced by a controlled surface fermentation of *Aspergillus oryzae* on a wheat bran koji culture, followed by extraction with water and then further purification. The peptidase FPII fraction was a white tan, free flowing powder with no offensive odor, had a protease activity of pH 7.0 of NLT 110,000 units/g, a peptidase activity of pH 5.0 of NLT 6,500 units/g, a drying loss of NMT 10%, a conditional loss of NMT 10%, heavy metals of NMT 50 PPM, arsenic of NMT 2 PPM, a total plate count of NMT 1,000/g, and was negative for coliforms. The protease activity was determined by a modification Anson-Hajiwara procedure using a Hammerstein casein substrate, while the peptidase activity was determined using synthetic substrate, H-Glu-Tyr-Glu-OH. The Peptidase FPII composition additionally comprised other enzyme activities, including an alkaline protease, a neutral protease, and endoproteases, as well as leucine amino peptidase. Optimum pH was about 6-9 and its stable pH was about 2.8-10.1.

Acid-stable protease ((25 SAPU) Spetrophotometric Acid Protease Units); Bio-Cat, Inc., Troy, Va., USA 22974, and National Enzyme Company, Forsythe, Mo., USA 65653), which is a protease having a higher activity profile at lower pH levels. This component 25 provided continued and additional proteolysis in the acid conditions of the stomach. The enzyme was manufactured with wheat bran culture of *Aspergillus* and was extracted with water and further purified using ethanol. It was a yellowish powder having an activity of 15,000 units/g wherein one unit of acid protease activity is defined as the quality of enzyme needed to produce amino acids equivalent to 100 µmol of tyrosine in 1 ml of filtrate per 60 minutes of 37° C and pH 3.0.

Protease 20,000 HUT (National Enzyme Company, Forsythe, Mo., USA 65653, and from Valley Research, Inc., South Bend, Ind., USA 46624 as Validase®FP 600).This enzyme was produced by a controlled fermentation of *Aspergillus oryzae* and contains both endopeptidase and exopeptidase activity. Endopeptidase hydrolyze the interior peptide bonds of protein liberating peptides of varying lengths, and the exopeptidase liberate amino acids by hydrolysis of the peptide bonds at the terminus of the peptide chain. The enzymes have a broad substrate specificity for, e.g., gluten, egg yoke, casein, soya, gelatin, hemoglobin and fish. It has an activity of 5,000,000 HUT/g, is in a light tan powder and is soluble in water. (One hemoglobin unit on the tyrosine basis (HUT/g) is that activity which produces, in one minute, hydrolysate that has an absorbency at 275 nm equivalent to that of a solution containing 1 µg/ml of tyrosine in 0.006 N hydrochloric acid.) This component had an optimum pH range of 2.5 to 6.0 30° C.

Lactase, 1,000 ALU (Acid Lactase Units; National Enzyme Company, Forsythe, Mo., USA 65653; Valley Reserch, Inc., South Bend, Ind., USA 46624). Lactase obtained by a fermination of *Aspergillus oryzae* and catalyzed the hydrolysis of lactose beta-D-galactoside linkage, liberating one mole of D-glucose and one mole of D-galactose, The component has 100,000 F.C.C. LU (F.C.C. lactase unit/g, is a light tan amorphous dry powder and is free of offensive odor and taste. 1 F.C.C. LU is that amount of enzyme that will liberate one micromole of o-nitrophenol per minute at pH 4.5 and 37° C. The lactase has an effective pH range of 3.5-6.5 and optimum pH range of 4.5-5.0.

Papain (sulfite free), 2,500,000 F.C.C. PU (Food Chemical Codex Plant Units; National Enzyme Company, Forsythe, Mo., USA 65653). Papain has a relatively broad substrate specificity including substrates containing a bulky non-polar side chain (such as phenyalanine) at the P2 position of a P1-P2 cleavage site.

L-lysine, 100/mg. L-lysine is an amino acid with alkaline properties. It is believed to provide a more alkaline microenvironment for the other enzymes while in the stomach, and thereby tends to increase enzyme activity.

EXAMPLE 2

Suitable proteases may be isolated from their native source or they may be produced via recombinant DNA technology by a suitable host cell, selected from any one of bacteria, yeast, fungi, plant, insect or mammalian host cells in culture. For examples, see U.S. Pat. No. 6,309,868 and Doumas et al., 1998. Recombinant enzymes encompass or are encoded by nucleic acids from a naturally occurring enzyme sequence. Further, recombinant enzymes include an amino acid sequence that is homologous or substantially identical to a naturally occurring sequence, as well as those enzymes encoded by a nucleic acid that is homologous or substantially identical to a naturally occurring protease-encoding nucleic acid. Alternatively, enzymes useful in the compositions and methods of this invention may be synthesized by conventional peptide synthesis techniques. Methods of producing and purifying enzymes, including proteases and peptidases, are known to those skilled in the art.

Many commercial suppliers sell purified proteases and peptidases that may be used in the invention. For a review, see Sumantha et al., 2006. A few examples of commercial suppliers are: Amano Enzyme Inc; Novozymes; and National Enzyme Company.

EXAMPLE 3

For administration of the compositions that are the subject of the invention as pharmaceuticals, numerous potential methods of protein stabilization, modification, and formulation are known to persons skilled in the art. See U.S. Pat. No. 6,613,332; US Patent Appl. 20080311214; US Patent Appl. 20080317726; Singh et al., 2008; McNally and Hastedt, 2008; Mahato, et al., 2003; Rao, 2008. These and other methods may be used in the present invention.

It should be emphasized that the methods of formulation and administration of the compositions and synergistic compositions are not limited to the examples provided herein; additional methods and novel formulations may be devised by persons skilled in the art.

The entire contents including the references cited therein of the following patents, published applications including all their foreign equivalents and journal publications are incorporated by reference in their entirety for all purposes to the same extent as if each individual patent, patent application or publication were so individually denoted.

| U.S. Pat. No. | Date | Inventor |
| --- | --- | --- |
| 3,932,618 | January, 1976 | Fujii, S |
| 5,296,223 | March, 1994 | Nakanishi, et al. |
| 5,324,514 | June 1994 | Sipos |
| 5,387,422 | February, 1995 | Handel, et al. |
| 5,750,650 | May, 1998 | Nakanishi, et al. |
| 6,251,391 | June, 2001 | Wilkinson, et al. |
| 6,309,868 | October, 2001 | Monod, et al. |
| 6,413,512 | July, 2002 | Houston |
| 6,447,772 | September 2002 | Houston |
| 6,613,332 | September 2003 | Michael, et al. |

-continued

| U.S. Pat. No. | Date | Inventor |
| --- | --- | --- |
| 6,808,708 | October, 2004 | Houston |
| 6,821,514 | November, 2004 | Houston |
| 6,844,180 | January 2005 | Oi, et al. |
| 6,899,876 | May, 2005 | Houston |
| 6,900,173 | May 2005 | Martin, et al. |
| 6,994,987 | February, 2006 | Yamamoto, et al. |
| 7,067,124 | June 2006 | Davidson, et al. |
| 7,141,582 | November, 2006 | Fan, et al. |
| 7,235,390 | June 2007 | Gibbs |
| 7,459,155 | December, 2008 | Margolin, et al. |
| 7,718,169 | May, 2010 | Margolin, et al. |

| U.S. Pat. applications | | |
| --- | --- | --- |
| 2003/0096392 | May 22, 2003 | Hunter, et al. |
| 2006/0062859 | Mar. 23, 2006 | Blum, et al. |
| 2008/0118492 | May 22, 2008 | Cerceo, J. |
| 2008/0311214 | Dec. 18, 2008 | Rao, K. |
| 2008/0317726 | Dec. 25, 2008 | Svendsen, A. |
| 2009/0155239 | Jun. 18, 2009 | Nakamura, T. |
| 2010/0120056 | May 13, 2010 | Bar-Or, D, and Bar-Or, R. |
| 2010/0196279 | Aug. 5, 2010 | Lockhart |

OTHER REFERENCES

1. Basten D E, et al. Characterisation of *Aspergillus niger* prolyl aminopeptidase. *Mol Genet Genomics* 2005; 272(6): 673-9.

2. Bergkvist R, Svard P O. Studies on the thrombolytic activity of a protease from *Aspergillus oryzae*. *Acta Physiologica Scandinavica* 1964; 60(4):363-371, 2008.

3. Bultron G, et al. The risk of Parkinson's disease in type 1 Gaucher disease. J Inherit Metab Dis. 2010; 33(2): 167-173.

4. Byun T, Kofod L, Blinkovsky A. Synergistic action of an X-prolyl dipeptidyl aminopeptidase and a non-specific aminopeptidase in protein hydrolysis. *J Agric Food Chem* 2001; 49(4):2061-3.

5. Castell J V, et al. Intestinal absorption of undegraded proteins in men: presence of bromelain in plasma after oral intake. *Am J Physiol Gastrointest Liver Physiol* 1997; 273: G139-G146.

6. Doumas A, et al. Characterization of the Prolyl Dipeptidyl Peptidase Gene (dppIV) from the Koji Mold *Aspergillus oryzae*. *Appl Environ Microbiol* 1998; 64(12):4809-4815.

7. Ehren J, et al. A Food-Grade Enzyme Preparation with Modest Gluten Detoxification Properties. *PLoS One* 2009; 4(7):e6313.

8. Frish, E. Clinical Review on Brinase, a Protease from *Aspergillus oryzae*. *Folia Haematol* 1974; 101(1):63-82.

9. Fujita, M., et al. Transport of nattokinase across the rat intestinal tract. *Biol Pharm Bull* 1995; 18(9):1194-1196.

10. Futerman A H, et al. New directions in the treatment of Gaucher disease. *Trends Pharmacol Sci* 2004; 25(3):147-151.

11. Goossens F, et al. Distribution of prolyl oligopeptidase in human peripheral tissues and body fluids. *Eur J Clin Chem Clin Biochem* 1996; 34:17-22.

12. Gotou T, et al. Purification and identification of proteolytic enzymes from *Aspergillus oryzae* capable of producing the antihypertensive peptide Ile-Pro-Pro. *J Biosci Bioeng* 2009; 107(6):615-9.

13. Harmanci O, Bayraktar Y. Gaucher disease: New developments in treatment and etiology. *World J Gastroenterol* 2008; 14(25): 3968-3973.

14. Hildebrandt M, et al. A guardian angel: the involvement of dipeptidyl peptidase IV in psychoneuroendocrine function, nutrition and immune defence. *Clin Sci (Lond)* 2000; 99(2):93-104.

15. Imamura K, Tsuyama Y, and Hirata T. Identification and characterization of a novel fermented substance produced by edible *Aspergillus oryzae* AO-1 that inhibits DPP-IV activity. *J. Biosci. Bioeng* 2010; In Press.

16. Jalving R, et al. Characterisation of the *Aspergillus niger* dapB gene, which encodes a novel fungal type IV dipeptidyl aminopeptidase. *Mol Genet Genomics* 2005; 273 (4):319-325.

17. Kolodny, A. Double blind evaluation of asperkinase, a new proteolytic enzyme. *Am J Orthopedics* 1963; 5:234-235.

18. Kreil G. Processing of precursors by dipeptidylaminopeptidases: a case of molecular ticketing. *Trends Biochem Sci* 1990; 15(1):23-26.

19. Kudryavtseva O A, et al. Fungal proteolytic enzymes: features of the extracellular proteases of xylotrophic basidiomycetes. *Microbiology* 2008; 77(6): 643-653.

20. Lambeir A M, et al. Dipeptidyl-peptidase IV from bench to bedside: an update on structural properties, functions, and clinical aspects of the enzyme DPP-IV. *Crit Rev Clin Lab Sci* 2003; 40(3):209-94.

21. Lesage S, Anheim M, Condroyer C, et al. Large-scale screening of the Gaucher's disease-related glucocerebrosidase gene in Europeans with Parkinson's disease. Hum Mol Genet. 2011; 20(1):202-10.

22. Lieberman J, Beutler E. Elevation of angiotensin-converting enzyme in Gaucher's disease. *N Engl J Med* 1976; 294:1442-1444.

23. Liu M, et al. The proteolytic system of lactic acid bacteria revisited: a genomic comparison. *BMC Genomics* 2010; 11:36.

24. Luisetti M, et al. Some properties of the alkaline proteinase from *Aspergillus melleus*. *Int J Tissue React* 1991; 13(4):187-92.

25. Machida M, Gomi K, eds. *Aspergillus:* Molecular Biology and Genomics. 2010; Caister Academic Press, UK.

26. Maes et al. Alterations in plasma prolyl endopeptidase activity in depression, mania, and schizophrenia: effects of antidepressants, mood stabilizers, and antipsychotic drugs. *Psychiatry Res* 1995; 58:217-225.

27. Mahato R I. Emerging trends in oral delivery of peptide and protein drugs. *Crit Rev Ther Drug Carrier Syst* 2003; 20(2&3):153-214.

28. Majima Y., et al. The effect of an orally administered proteolytic enzyme on the elasticity and viscosity of nasal mucus. *Arch Otorhinolaryngol* 1988; 244(6):355-359.

29. Mantle et al. Comparison of proline endopeptidase activity in brain tissue from normal cases and cases with Alzheimer's disease, Lewy body dementia, Parkinson's disease and Huntington's disease. *Clin Chim Acta* 1996; 249: 129-139.

30. Maurer H R. Bromelain: biochemistry, pharmacology and medical use. *Cell Mol Life Sci* 2001; 58 (9):1234-1245.

31. McNally E J, Hastedt J E, eds. Protein formulation and delivery. 2nd edition. 2008, Informa Healthcare USA Inc.

32. Meyer V, Wu B, Ram A F. *Aspergillus* as a multipurpose cell factory: current status and perspectives. *Biotechnol Lett* 2010 Nov. 19. [Epub ahead of print]

33. Mitea C, et al. Efficient degradation of gluten by a prolyl endoprotease in a gastrointestinal model: implications for coeliac disease. *Gut* 2008; 57(1):25-32.

34. Miyata K, et al. Serratia protease part I. Purification and general properties of the enzyme. *Agr Biol Chem* 1970; 34(2): 310-318.

35. Neudorfer O, et al. Occurrence of Parkinson's syndrome in type I Gaucher disease. QJM: monthly journal of the Association of Physicians. 1996; 89(9):691-4.

36. O'Toole, D K. Characteristics and use of okara, the soybean residue from soy milk production—a review. *J Agric Food Chem* 1999; 47(2):363-371.

37. Pal A, et al. Structure of tripeptidyl-peptidase I provides insight into the molecular basis of late infantile neuronal ceroid lipofuscinosis. *J Biol Chem* 2009; 284(6):3976-3984.

38. Pant K K, et al. Parflex—a very useful drug for management of surgical pain. *J Indian Med Assoc* 2008; 106(6): 409-411.

39. Peng et al. Microbial fibrinolytic enzymes: an overview of source, production, properties, and thrombolytic activity in vivo. *Appl Microbiol Biotechnol* 2005; 69:126-132.

40. Rao M B, et al. Molecular and biotechnological aspects of microbial proteases. *Microbiol Mol Biol Rev.* 1998; 62(3): 597-635

41. Reichard U, et al. Sedolisins, a new class of secreted proteases from *Aspergillus fumigatus* with endoprotease or tripeptidyl-peptidase activity at acidic pH. *Appl Environ Microbiol* 2006; 72(3):1739-1748.

42. Rogers D F. Mucoactive agents for airway mucus hypersecretory diseases. *Respir Care* 2007; 52(9):1176-93.

43. Rosenblum J S, Kozarich J W. Prolyl peptidases: a serine protease subfamily with high potential for drug discovery. *Curr Opin Chem Biol* 2003; 4:496-504.

44. Sedo et al. Dipeptidyl peptidase IV, prolyl endopeptidase and cathepsin B activities in primary human lung tumours and lung parenchyma *J Cancer Res Clin Oncol* 1991; 117:249-253.

45. Singh R, et al. Past, present, and future technologies for oral delivery of therapeutic proteins. *J Pharm Sci* 2008; 97:2497-2523.

46. Sriranganadane D, et al. Aspergillus protein degradation pathways with different secreted protease sets at neutral and acidic pH.—*J Proteome Res.* 2010; 9(7):3511-9.

47. Sumantha A, et al. Microbiology and industrial biotechnology of food grade proteases. *Food Technol Biotechnol* 2006; 44(2):211-220.

48. Sumi H, et al. Enhancement of the fibrinolytic activity in plasma by oral administration of nattokinase. *Acta Haematol* 1990; 84(3):139-143.

49. Tachi H, Ito H, Ichishima E. An X-prolyl dipeptidylaminopeptidase from *Aspergillus oryzae*. *Phytochemistry* 1992; 31:3707-3709.

50. Yoshida, K. Sfericase, a novel proteolytic enzyme. *Int J Clin Pharmacol Ther Toxicol* 1983; 21(9):439-46.

Although the present invention has been described with reference to specific details of certain embodiments thereof, it is not intended that such detail should be regarded as limitations upon the scope of the invention, except as and to the extent that they are included in the accompanying claims.

What is being claimed is:

1. A method for reducing splenomegaly and increasing energy in patients with Gaucher disease, which method comprises orally administering to an individual in need thereof an effective amount of a pharmaceutically acceptable composition comprising a blend of the proteolytic enzymes comprising peptidase FPII comprising casomophinase having DPP-IV activity, obtained by surface fermentation of *Aspergillus oryzae* and having an activity of 25,000 hemoglobin units of tyrosine (HUT), acid-stable protease manufactured from wheat bran culture of *Aspergillus* and having 25 spectrophotometric acid protease units, protease from the fermentation of *Aspergillus oryzae*, containing both endo and exo-peptidase activity and having an activity of 20,000 HUT, lactase from the fermentation of *Aspergillus oryzae* and having 1,000 acid lactase units;

papain having 2,500,000 food chemical codex plant units; and l-lysine in an amount sufficient to reduce said splenomegaly and increase energy in said patients; and wherein said proteolytic enzyme blend has 54,000 hemoglobin units on a tyrosine basis, 130 units of aminopeptidase activity and 50 spectrophotometric acid protease units.

2. The method of according to claim 1, wherein the enzyme blend is derived from a fermented food or beverage.

3. The method according to claim 1, wherein the enzyme blend is derived from a food-grade microorganism, yeast, algae, seaweed, plant, vertebrate animal, invertebrate animal, annelid, insect, or arthropod.

4. The method according to claim 1, wherein the enzyme blend is derived from a species of *Aspergillus*.

5. The method according to claim 1, wherein the pharmaceutically acceptable composition is labeled as a dietary supplement.

6. The method according to claim 5, wherein the pharmaceutically acceptable composition is formulated as a dried powder, a tablet, a hard gelatin capsule or a soft gelatin capsule.

7. The method according to claim 5, wherein the pharmaceutically acceptable composition is provided within an ingestible carrier material suitable for human consumption.

8. The method of claim 7, wherein the carrier material is selected from the group consisting of a cereal based product, rice cake, soy cake, food bar product, cold formed food bar product, custard, pudding, gelatin, rice milk, soy milk, mashed fruit product, candy, candy bar, applesauce, yogurt, beverage, and fermented beverage.

9. The method according to claim 6, 7 or 8 wherein the pharmaceutically acceptable composition further contains one or more of the following ingredients selected from the group consisting of: vitamins, minerals, herb or herbal extracts, probiotics or prebiotics, antioxidants, bioflavonoids, papain, lactase, amylase, protease, lipase, and plant and animal concentrates.

10. The method according to claim 1, wherein the pharmaceutically acceptable composition is administered in combination or in conjunction with a separate, FDA-approved pharmaceutical composition.

11. The method according to claim 1, wherein the pharmaceutically acceptable composition further contains a therapeutically-active small molecule.

12. The method according to claim 10, wherein the FDA-approved pharmaceutical composition is a therapeutically-active small molecule.

* * * * *